United States Patent [19]

Kaplan et al.

[11] Patent Number: 5,455,270

[45] Date of Patent: Oct. 3, 1995

[54] STABILIZED SOLUTIONS OF PLATINUM(II) ANTITUMOR AGENTS

[75] Inventors: Murray A. Kaplan, Syracuse; Lawan Phusanti, Lafayette; Robert K. Perrone, Liverpool; Scott R. Stenberg, Baldwinsville; Sheeram Agharkar, Fayetteville; Joseph B. Bogardus, Manlius, all of N.Y.

[73] Assignee: Bristol-Myers Squibb Co., New York, N.Y.

[21] Appl. No.: 105,817

[22] Filed: Aug. 11, 1993

[51] Int. Cl.$^6$ ............................. A61K 31/28; C07F 15/00
[52] U.S. Cl. ................................. 514/492; 556/137
[58] Field of Search .................... 514/492; 556/137

[56] References Cited

U.S. PATENT DOCUMENTS

| 4,140,707 | 2/1979 | Cleare et al. |
| 4,657,927 | 4/1987 | Cleare et al. |
| 5,104,896 | 4/1992 | Nijkerk et al. |
| 5,288,887 | 2/1994 | Khobhar et al. ............ 516/137 |

FOREIGN PATENT DOCUMENTS 0334551  9/1989  European Pat. Off.

OTHER PUBLICATIONS

Pasini, A. et al. Inorganica Chimica Acta 151 (1988) pp. 19–20.
Khokhar, A. et al. J. of Inorganic Biochemistry, 50, 79–87 (1993).
Cancer Chemother Pharmacel, (1989), 23: 197–207.

Primary Examiner—Paul J. Killos
Attorney, Agent, or Firm—Sandra M. Nolan

[57] ABSTRACT

Solutions of carboplatin and other malonato platinum(II) antitumor agents are prepared containing stabilizing amounts of 1,1-cyclobutanedicarboxylic acid or salt at pH 4–8. The stabilizers inhibit unacceptable discoloration and precipitation. The solutions may also be stabilized by purging the carrier with air or oxygen and, optionally, blanketing the headspace with air or oxygen.

16 Claims, No Drawings

STABILIZED SOLUTIONS OF PLATINUM(II) ANTITUMOR AGENTS

BACKGROUND

Carboplatin, 1,1-cyclobutanedicarboxyl diammine platinum-(II), is a white to off-white crystalline powder. Like cisplatin, it is a cytotoxic platinum coordination compound. Also like cisplatin, it has cytotoxic properties which render it useful in the treatment of various malignancies in mammals, including ovarian carcinoma.

U.S. Pat. Nos. 4,140,707 and 4,657,927 to Cleare et al disclose the preparation of carboplatin and other malonato platinum compounds and their use in treating a standard screening tumor, solid sarcoma 180. This group of compounds may be termed "malonato" because of the presence in their structures of a —(OOC)$_2$—C< linkage.

Unlike cisplatin, carboplatin does not generally produce severe side effects, such as renal toxicity, ototoxicity and neurotoxicity. Carboplatin resists aquation, which thus contributes to its lower toxicity. It has been used to treat a variety of human cancers, including small cell lung cancer, squamous cell carcinomas and testicular cancer. See *U.S. Pharmacist*, September, 1989, pages 62–63.

Carboplatin is sold as a lyophilized powder usually diluted with water, saline solution, dextrose solution and/or other diluents just before intravenous injection into a patient. However, its relatively low solubility in water (14 mg/ml at room temperature) may lead to problems, e.g., "splash back" during reconstitution. It, like all anti-neoplastic agents, can have undesirable effects when in contact with normal tissue.

A solution of carboplatin, in a concentrated ready-to-use (RTU) form would be very desirable to facilitate handling and administration. However, the compound is not physically stable over prolonged storage in simple aqueous solutions—i.e., when mixed with water alone.

U.S. Pat. No. 5,104,896 to Nijkerk et al discloses an attempt to address this problem. Theirs are carboplatin solutions containing up to 22 mg/ml carboplatin and 0.01–0.1 moles of inorganic-buffering agents to maintain a solution pH of 2 to 6.5.

A. Bosonquet, in *Cancer Chemother Pharmacol*, 23: 197–207 (1989), discussed the instability of carboplatin and suggested that water and sodium chloride be used to produce stable solutions of same. Levius et al, in E.P.O. Publication 334,551 (published Sep. 21, 1989) suggest that chloride ions should not be used in carboplatin solutions (see page 3, lines 7+). Furthermore, they teach that aqueous carboplatin solutions, containing 10–15 mg/ml of the drug, are stable if the drug has not been lyophilized and the water is salt-free (see page 2, lines 22+).

THE INVENTION

The invention is concerned with stable carboplatin compositions, methods of making same and stable products based on those compositions and methods.

Applicants have discovered that stable, 1,1-cyclobutanedicarboxylic acid (CBDCA) buffered solutions of carboplatin can be made using, as stabilizers, one or more of:

(1) 1,1-cyclobutanedicarboxylic acid, (to pH 4–8), (2) purging the solution with air or oxygen, and (3) blanketing the head space in the vial or other container with air or oxygen.

In highly preferred embodiments, all three of (1), (2) and (3) are employed. The resultant solutions have a pH of about 4 to about 8, contain about 1 to about 15 mg/ml carboplatin, include a carrier containing water, and are stored in vials that have a 50 volume percent headspace. The solutions are chemically and physically stable for at least 4 months at 50° C.

ADVANTAGES

The compositions, products, and methods of the invention have several advantages over the prior art.

The "splash back" and other problems associated with the use of a lyophilizate or other powdered form of carboplatin are eliminated by using dilutable solutions of ready-to-use (RTU) injectable formulations.

The RTU formulations, which are less expensive to manufacture, will require no additional preparation or handling, other than dilution, before administration.

The stability of the new formulations, i.e., up to 18 months at 24° C., or ambient temperatures means that they need not be checked for expiration dates and discarded as frequently as previous formulations were.

With minimal precautions regarding temperature and light sensitivity, the carboplatin solutions described herein are easy to use and maintain.

These and other advantages will become more evident upon consideration of the following specification and claims.

DESCRIPTION OF THE INVENTION

Unless stated otherwise, all percentages recited herein are weight percents, based on total composition weight.

All publications referred to are hereby incorporated by reference.

In all tables herein, the term "clear", "no precipitates" and "no precipitate" are synonymous.

The Active Component

The active component used herein is one or more malonato platinum(II) compounds.

While "carboplatin" is referred to throughout the specification, applicants intend that this term include all coordination compounds containing two monodentate ammonia or amine ligands and one bidentate molanato ligand bearing a 1,1-cycloalkyldicarboxylic acid residue.

Suitable compounds conform to formula I:

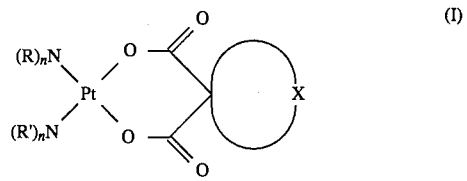

wherein:

R and R$^1$ are independently selected from H, C$_{1-6}$ alkyl, C$_{1-6}$ hydroxyalkyl, C$_{5-12}$ aryl, C$_{5-12}$ alkaryl, C$_{5-12}$ aralkyl, C$_{1-6}$ alkoxyalkyl and C$_{5-12}$ amino acid residues;

n is 2 or 3; and

X is the residue of a cyclic C$_{3-6}$ alkyl or alkenyl group.

It is preferred that R=R'=H, that n=3 and that X be a cycloalkyl moiety.

It is highly preferred that carboplatin (of structure II), as well as isomers and conventional derivatives thereof, be used. Structure II is:

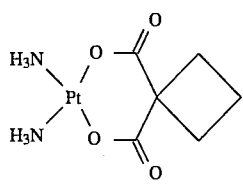

By "conventional derivatives", applicants mean solvates, complexes, hydrates, geometric isomers, analogs having substituted nucleii and the like.

Cisplatin and other therapeutic compounds useful herein can be prepared by the method disclosed in U.S. Pat. Nos. 4,140,707, and 4,657,927.

The general reaction scheme is:

cis-[Pt ACl2]+2AgNO3+2H2O→cis-[Pt A(H2O)2](NO3)2+2AgCl cis-[Pt A(H$_2$O)$_2$](NO$_3$)$_2$+X(COOH)$_2$→[Pt A(OOC)$_2$—CH$_2$]+ 2NO$_3^-$+2H$_2$O+2H$^+$ wherein A is one bidentate amine ligand or two monodentate amine ligands and X is as defined above.

The utility of carboplatin as an anti-neoplastic agent is well known.

The Stabilizing Systems (1) 1,1-Cyclobutanedicarboxylic acid (CBDCA) and Salts

The acid CBDCA is a reactant in a preferred process of making carboplatin. It is a water-soluble constituent of unstabilized solutions of same.

Useful salts of CBDCA include the alkali metal salts. The sodium salt is preferred, especially when the carrier is water or one or more polyalkylene glycols.

CBDCA and its sodium salt were once studied as buffers for carboplatin because of their high miscibility with the drug. However, the acid and its salts have not been previously disclosed as stabilizers for platinum(II) compounds.

In some preferred embodiments, this stabilizer system involves the use of CBDCA as a stabilizer along with its sodium salt as a pH modifier.

The acid or one or more salts are added to solutions of carboplatin or other malonato platinum(II) compounds in quantities sufficient to yield final CBDCA concentrations of about 0.25 to about 4 mg/ml at a pH of about 4 to about 8. Preferred quantities are about 1 to about 2 mg/ml.

(2) Air or Oxygen Purging

The use of air—i.e., a gaseous mixture, at room temperature, of about 78% nitrogen and about 21% oxygen—or pure oxygen ($O_2$) is contemplated. Oxygen is a preferred purging agent.

Mixtures of oxygen and air may be employed. It is preferred that the oxygen content of such mixtures be between about 25% and about 95%. Nonnitrogenous gases, such as argon, can also be used.

The use of nitrogen concentrations of more than about 78% in the purging gas is to be avoided.

By "purging" applicants mean bubbling or otherwise passing the desired gas through the solution under atmospheric pressure to saturate the liquid and headspace with optimum quantities of oxygen.

The duration of the purging step is not critical. However, it is generally desirable to purge the drug-containing liquid solutions for periods of about 1 to about 5 hours. Two hours is typical. Ambient, or room, temperatures, of about 25° to 30° C., are typically employed.

When a purging technique is employed, it is preferred (but not required) that the liquid in the container fill no more than 50% of its total volume (half full), that is, that the unfilled air oxygen volume, or headspace, be 50% or more of the total (liquid & gaseous) volume of the container.

(3) Blanketing the Headspace with Air or Oxygen

Filling the headspace, i.e., the space above the liquid volume, in the container with air or oxygen is another stabilizing method. Termed "blanketing", this technique involves pushing all ambient or atmospheric gases out of the space above the air or oxygen saturated liquid in the vial, bottle or other closed container. Immediately thereafter, the container is sealed.

The period for which the headspace is blanketed is generally between about 1 and about 5 hours. Periods of about 2 to about 3 hours are preferred.

As was stated above for the purging step, the use of gases containing more than 78% nitrogen must be avoided.

Each of these three techniques may be used alone to stabilize solutions containing carboplatin or other similar platinum(II) drugs having malonato linkages. However, it is preferred that techniques (1) and (2) be used together or that (2) and (3) be used together. It is highly preferred that all three be used together.

Carriers

The carriers to be employed as solvents for the platinum(II) compounds are generally water containing ones. Pure water (e.g., sterile water for injection) is preferred.

Mixtures of water and one or more auxiliary carriers, e.g., certain polyalkylene glycols and sugar solutions, can be used. Typically, the final water content in the solutions of the invention will range from about 0.5 to about 99.5%, with auxiliary carriers, e.g., glycols, being used at levels of about 10 to about 90% by weight, based on total carrier content.

Suitable glycols include polyalkylene glycols having molecular weights of about 300 to about 900 and being based on $C_{1-6}$ alkyl groups. Accordingly, polyether polyols, such as polyethylene glycols, polypropylene glycol, polybutylene glycol and the like and mixtures thereof can be used.

Polypropylene glycol and polyethylene glycol (PEG-400) are preferred. A mixture of 15 vol % water and 85 vol % of either PEG-400 or 85 vol % propylene glycol is highly preferred.

"Sugar solutions" includes solutions of pharmaceutically acceptable dextrose, sucrose, mannose or other sugars which function as isotonicity adjusting agents. 5% dextrose in water ("D5W") is one highly preferred auxiliary carrier.

The solutions of the invention may be supplied in both aqueous and nonaqueous concentrated RTU forms. Accordingly, the use of suitable amounts of auxiliary carrier(s) is optional. Other carriers which do not adversely affect the usefulness of the platinum compounds or the effectiveness of the stabilizers can be employed to replace all or part of the carrier(s) described above.

Buffers

The platinum II) compounds used herein are less subject to reductive degradation because of the use of one or more of techniques (1), (2) or (3). However, the stability of solutions of these compounds is further enhanced by the presence therein of one or more pH modifiers, which keep the solution pH within an optimal range and, thus, operate as buffers.

It is generally desirable that the pH of the solutions be between about 4 and about 7.

The ambient pH of carboplatin alone is about 6.5. Addition of CBDCA reduces it unacceptably to a pH below 4. Accordingly, the use of a basic buffer or pH modifier, to raise the pH, is needed.

Generally, buffers will be simple inorganic bases whose cationic portions are pharmaceutically acceptable. Thus, oxides and hydroxides of sodium, potassium and calcium are useful. Sodium hydroxide is preferred.

The optimal amount of sodium hydroxide or other buffer is found by titrating the CBDCA/platinum(II) compound mixture until a stable pH of about 4 to about 8, preferably about 5 to about 7 and most preferably about 5.5 to about 6.5, is attained.

Since the presence of both a basic additive and CBDCA is needed to reach the desired solution pH, the CBDCA may be considered a "buffer". However, the primary function of the CBDCA in applicant's systems is as a stabilizer for the carboplatin or other platinum(II) compound(s).

Administration

The dosage levels at which the formulations of the invention are used are generally dictated by sound medical judgment and other guiding principles, such as those set out in the *Physician's Desk Reference*.

Generally, the solutions will be administered to animals, preferably human beings, to treat cancer. Typically, the dosages will range from about 1 to about 200 mg/kg/dose, with about 1 to about 3 doses given periodically.

The solutions are adapted for administration by intravenous injection. They are supplied as ready-to-use concentrated (RTU) solutions. These concentrates are to be diluted with 1 to 60 volumes of water or another suitable diluent before injection.

While injection is a preferred route of administration, other routes, e.g., oral, are contemplated.

Storage

The long-term stability of platinum(II) anti-cancer agents is one principal purpose for this invention. Accordingly, conditions which are known to hasten the degradation of these compounds should be avoided. Excessive light, low pH (less than 4) and high temperatures are three such conditions.

The stability of the instant compositions at accelerated temperatures up to about 60° C. is discussed herein. Samples have been tested and found stable for periods of several weeks up to a year at 25° C.

The slight color changes which occur in some highly stressed solutions are usually not indicative of significant decreases of drug potency safety or efficacy. However, the use of solutions which are hazy or ones containing precipitate particles is not advised. Such particles can interfere with intravenous administration.

EXAMPLES

The following examples serve to illustrate the invention.

Example 1

Effect of 1,1-cyclobutanedicarboxylic acid (CBDCA) Concentration on Aqueous Solution Stability The effect of CBDCA concentration on the stability of carboplatin was evaluated at 50° C. and 60° C. Aqueous ~10 mg/mL carboplatin solutions were prepared with CBDCA concentrations of 8, 4, 2, 1, 0.5, 0.25, and 0 mg/mL.

The pH of each solution containing CBDCA was adjusted to 6.0 with NaOH. The pH of each solution without CBDCA was not adjusted. The ambient pH of carboplatin is ~6.1 and varies from 5.5 to 7.0.

The solutions were then purged (bubbled) with air and filtered into washed #04515/00 Wheaton 6 mL vials using 10 mL disposable syringes and Gelman #4192 sterile 0.2 μm filters. Each vial contained three milliliters of the solution, leaving approximately 50% air headspace. All test vials were stoppered with Daikyo #759 fluororesin coated stoppers and sealed with Wheaton 20 mm aluminum closures.

Long term stability samples at 25° C. and 40° C. (8½ months and 9 months) were conducted. Data for these samples are:

Tables 1

Carboulatin Physical Stability at 25° C. and 40° C.

Table 1A:
Effect of Various Levels of CBDCA* and Headspace Gas on the Chemical and Physical Stability of Aqueous 10 mg/mL Solutions of Carboplatin at pH 6

CBDCA Experiment Group I; 8 months, 16 days at 25° C.: 50% Air Headspace

| CBCDA Concentration (mg/ml) | Solution Color | Solution Clarity |
|---|---|---|
| 8 | colorless | no precip. |
| 4 | colorless | no precip. |
| 2 | colorless | no precip. |
| 1 | colorless | no precip. |
| 0.5 | colorless | no precip. |
| 0.25 | colorless | no precip. |
| 0 | straw | no precip. |

Group II, 8 months, 16 days at 25° C.: various Headspace Gases

| Headspace Gas | CBDCA (mg/ml) | Solution Color | Solution Clarity |
|---|---|---|---|
| $N_2$ | 1 | Straw | no precip. |
| Air | 1 | colorless | no precip. |
| $O_2$ | 1 | colorless | no precip. |
| $N_2$ | 0 | amber | no precip. |
| Air | 0 | straw | no precip. |
| $O_2$ | 0 | colorless | no precip. |

Table 1B:
Effect of Vial Fill Volume on the 25° C. Chemical and Physical Stability of Aqueous 10 mg/mL Solutions of Carboplatin at pH 6 ± 1 mg/mL CBDCA* With air Headspace*
(Air Purged Solutions)
Group III., 9 months, 3 days at 25° C.: various fill volumes

| Vial Fill Volume (ml) | CBDCA (mg/ml) | Solution Color | Solution Clarity |
|---|---|---|---|
| 2 | 1 | colorless | no precip. |
| 4 | 1 | colorless | no precip. |
| 6 | 1 | colorless | no precip. |
| 8 | 2 | colorless | no precip. |
| 10 | 1 | colorless | no precip. |
| 12 | 1 | colorless | no precip. |
| 2 | 0 | colorless | no precip. |
| 4 | 0 | colorless | no precip. |
| 6 | 0 | colorless | no precip. |
| 8 | 0 | colorless | no precip. |
| 10 | 0 | straw | no precip. |
| 12 | 0 | straw | no precip. |

Table 1C:
Effect of pH on the Chemical and Physical Stability of Aqueous, 10 mg/mL solutions of Carboplatin containing 1 mg/mL CBDCA* With Air Headspace *
Group IV., 9 months, 27 days at 25° C.: variable pH

| pH | Solution Color | Solution Clarity |
|---|---|---|
| 4 | colorless | no precip. |
| 5 | colorless | no precip. |
| 6 | colorless | no precip. |
| 7 | colorless | no precip. |

Tables 1-continued

Carboulatin Physical Stability at 25° C. and 40° C.

| | | | |
|---|---|---|---|
| 8 | colorless | | no precip. |

Table 1D:
Effect of CBDCA Concentration on 6 months and 8 weeks
Stability at 40° C. Fresh carbolatin with varying concentrations
of cyclobutanedicarboxcylic Acid (CBCDA) were used. Samples
were pH adjusted with NaOH and purged with air. Each sample
vial contained 3.3 ml of carboplatin solution in a 6 ml
Type I glass vial. Vial headspace was filled with air.

| CBDCA (mg/ml) | Appearance | pH | Conc. (mg/ml) | Carboplatin % remaining |
|---|---|---|---|---|
| Group I - 6 months | | | | |
| 8 | Clear | 6.00 | 10.071 | 104.4 |
| 4 | Clear | 6.01 | 9.887 | 99.4 |
| 2 | Clear | 6.03 | 9.97 | 100.6 |
| 1 | Clear | 6.04 | 9.944 | 97.4 |
| 0.5 | Straw | 6.09 | 9.999 | 104.3 |
| 0.25 | Straw | 6.03 | 9.915 | 98.9 |
| 0 | Yellow | 5.85 | 9.946 | 99.0 |
| Group II - 8 weeks | | | | |
| 8 | Clear | 6.13 | 9.921 | 102.8 |
| 4 | Clear | 6.09 | 10.014 | 100.7 |
| 2 | Clear | 6.08 | 10.004 | 100.9 |
| 1 | Clear | 6.07 | 10.044 | 98.4 |
| 0.5 | Clear | 6.18 | 10.136 | 105.7 |
| 0.25 | Clear | 6.16 | 10.077 | 100.5 |
| 0 | Clear | 6.13 | 10.08 | 100.4 |

Table 1E:
Effect of Fill Volume on 6 month 40° C. Stability

| Liquid Fill Volume (mL) | Appearance | CBDCA (mg/ml) | pH | Carbo-platin Conc. (mg/mL) | % remaining |
|---|---|---|---|---|---|
| Group I - (See Note I) | | | | | |
| 12 | Straw - no precip. | 1 | 5.99 | 9.273 | 95.8% |
| 10 | Straw - no precip. | 1 | 6.09 | 9.342 | 96.5% |
| 8 | Straw - no precip. | 1 | 6.10 | 9.183 | 94.9% |
| 6 | Straw - no precip. | 1 | 6.11 | 9.276 | 95.9% |
| 4 | Straw - no precip. | 1 | 6.11 | 9.322 | 96.3% |
| 2 | Straw - no precip. | 1 | 6.18 | 9.421 | 97.4% |
| Group II - (See Note II) | | | | | |
| 12 | Amber - no precip. | 0 | 5.68 | 9.602 | 97.2% |
| 10 | Amber - no precip. | 0 | 5.60 | 9.533 | 96.5% |
| 8 | Amber - no precip. | 0 | 5.63 | 9.496 | 96.1% |
| 6 | Amber - no precip. | 0 | 5.58 | 9.321 | 94.4% |
| 4 | Amber - no precip. | 0 | 5.61 | 9.457 | 95.7% |
| 2 | Amber - no precip. | 0 | 5.65 | 9.806 | 99.3% |

Note I: Fresh 10 mg/ml solutions with 1 mg per ml of
cyclobutanedicarboxylic Acid (CBDCA) pH was adjusted to 6.2
with NaOH.
All samples were air purged and filled to the volume indicated.
Note II: Fresh 10 mg/ml Carboplatin solution (no CCBDCA)
pH was ambient (not adjusted). All samples were air purged
and filled to the volume TABLE 1F:
Effect of pH on 6 month 40° C. Solution Stability
Fresh 10 mg/ml carboplatin solutions were prepared with 1 mg
per ml of cyclobutanedicarboxylic acid (CBDCA). pH was
varied with each sample and adjusted with NaOH.
All samples were air purged and filled to 3.3 ml in a
ml Type I glass vial. Vial headspace was filled with air.
Sample number denotes starting pH. 1 mg/ml CBDCA was
used in all samples.

| pH | Appearance | pH | Carboplatin Conc.(mg/mL) | % remaining |
|---|---|---|---|---|
| 4 | Straw - no precip. | 4.13 | 10.060 | 96.4 |
| 5 | Clear - no precip. | 5.06 | 10.141 | 97.1 |
| 6 | Clear - no precip. | 6.07 | 9.986 | 96.4 |
| 7 | Clear - no precip. | 6.75 | 9.713 | 89.6 |
| 8 | Straw - no precip. | 6.99 | 9.015 | 92.6 |

All samples were assayed by HPLC to determine initial carboplatin concentration. At the designated intervals, appearance (i.e., visual clarity, presence of precipitate, color) and pH of each stability sample was recorded. The samples were then assayed for carboplatin. Based on initial values, percent carboplatin remaining was then calculated for each sample.

TABLE 2

| HPLC Method for the Quantitative Assay of Carboulatin | |
|---|---|
| COLUMN: | Alltech 10 micron $NH_2$, 4.6 × 250 mm |
| DETECTION: | 230 rim |
| INJECTION VOLUME: | 20 microliter |
| SAMPLE CONC.: | Approximately 1 mg/mL |
| DILUENT: | Milli-Q Water |
| EXTERNAL STANDARD: | Approximately 1 mg/mL Carboplatin |
| TEMPERATURE: | 30° C. |
| MOBILE PHASE: | 85% Acetonitrile / 15% Milli-Q Water |
| FLOW RATE: | 2.0 mL/min. |
| RUN TIME: | 15–18 minutes |
| TYPICAL RETENTION TIMES: | Carboplatin 10 minutes |

Samples were stored at 60° C. for 1, 2, 4, and 8 weeks, and at 50° C. for 2, 4, 8, and 16 weeks. Data for these samples are given in Tables 3 and 4.

TABLE 3

Effect of Various Levels of CBDCA* on the Chemical and Physical Stability of Aqueous 10 mg/mL Solutions of Carboplatin at pH 6 with 50% Air Headspace

| Storage Conditions | CBDCA (mg/mL) | pH | Carboplatin mg/mL | Carboplatin % Rem. | Solution Color | Solution Clarity |
|---|---|---|---|---|---|---|
| Original | 8 | 6.00 | 9.65 | 100 | colorless | clear |
| Original | 4 | 6.00 | 9.94 | 100 | colorless | clear |
| Original | 2 | 6.01 | 9.91 | 100 | colorless | clear |
| Original | 1 | 6.00 | 10.21 | 100 | colorless | clear |
| Original | 0.5 | 6.08 | 9.59 | 100 | colorless | clear |
| Original | 0.25 | 6.06 | 10.03 | 100 | colorless | clear |
| Original | 0 | 7.17 | 10.05 | 100 | colorless | clear |
| 1W60° C. | 8 | 6.08 | 9.86 | 102.2 | colorless | clear |
| 1W60° C. | 4 | 6.09 | 9.79 | 98.5 | colorless | clear |
| 1W60° C. | 2 | 6.12 | 9.87 | 99.6 | colorless | clear |
| 1W60° C. | 1 | 6.01 | 9.9 | 96.9 | colorless | clear |
| 1W60° C. | 0.5 | 6.09 | 9.84 | 102.6 | colorless | clear |
| 1W60° C. | 0.25 | 6.25 | 9.93 | 99.1 | colorless | clear |
| 1W60° C. | 0 | 6.52 | 9.85 | 98.1 | straw | clear |
| 2W60° C. | 8 | 5.96 | 9.51 | 98.6 | colorless | clear |
| 2W60° C. | 4 | 5.95 | 9.89 | 99.4 | colorless | clear |
| 2W60° C. | 2 | 5.98 | 9.61 | 96.9 | colorless | clear |
| 2W60° C. | 1 | 6 | 9.66 | 94.6 | colorless | clear |
| 2W60° C. | 0.5 | 6.03 | 9.65 | 100.6 | colorless | clear |
| 2W60° C. | 0.25 | 5.93 | 9.31 | 92.9 | colorless | clear |
| 2W60° C. | 0 | 5.59 | 9.72 | 96.7 | yellow | clear |
| 4W60° C. | 8 | 6.22 | 8.83 | 91.5 | straw | clear |
| 4W60° C. | 4 | 6.17 | 9.09 | 91.4 | straw | clear |
| 4W60° C. | 2 | 6.15 | 9.14 | 92.2 | straw | clear |
| 4W60° C. | 1 | 6.1 | 9.29 | 91 | yellow | clear |
| 4W60° C. | 0.5 | 6.09 | 9.26 | 96.5 | yellow | clear |
| 4W60° C. | 0.25 | 5.97 | 9.29 | 92.7 | yellow | clear |
| 4W60° C. | 0 | 5.52 | 9.28 | 92.4 | amber | hazy w/precipitate |
| 8W60° C. | 8 | 6.17 | 8.16 | 84.6 | straw | clear |
| 8W60° C. | 4 | 6.12 | 8.58 | 86.3 | straw | clear |
| 8W60° C. | 2 | 6.05 | 8.58 | 86.5 | straw | clear |
| 8W60° C. | 1 | 5.99 | 8.61 | 84.3 | yellow | clear |
| 8W60° C. | 0.5 | 5.94 | 8.76 | 91.3 | yellow | clear |
| 8W60° C. | 0.25 | 5.85 | 8.95 | 89.3 | amber | clear |
| 8W60° C. | 0 | 5.59 | 8.85 | 88.1 | brown | hazy w/precipitate |

*1.1-Cyclobutanedicarboxylic acid; 3.3 mL of solution per 6 cc Type 1 glass vial with 20 mm teflon-faced stopper; solution adjusted to pH 6 with NaOH.

TABLE 4

Effect of Various Levels of CBDCA* on the Chemical and Physical Stability of Aqueous 10 mg/mL Solutions of Carboplatin at pH 6 with 50% Air Headspace.

| Storage Conditions | CBDCA (mg/mL) | pH | Carboplatin mg/mL | % Rem | Solution Color | Solution Clarity |
|---|---|---|---|---|---|---|
| 2 W 50° C. | 8 | 5.91 | 9.13 | 94.6 | colorless | clear |
| 2 W 50° C. | 4 | 5.91 | 9.49 | 95.5 | colorless | clear |
| 2 W 50° C. | 2 | 5.91 | 9.03 | 91.1 | colorless | clear |
| 2 W 50° C. | 1 | 5.88 | 9.51 | 93.2 | colorless | clear |
| 2 W 50° C. | 0.5 | 5.99 | 9.88 | 103 | colorless | clear |
| 2 W 50° C. | 0.25 | 6.01 | 9.54 | 95.1 | colorless | clear |
| 2 W 50° C. | 0 | 5.88 | 9.66 | 96.2 | straw | clear |
| 4 W 50° C. | 8 | 6.17 | 9.63 | 99.7 | colorless | clear |
| 4 W 50° C. | 4 | 6.11 | 9.71 | 97.7 | colorless | clear |
| 4 W 50° C. | 2 | 6.13 | 9.71 | 98 | colorless | clear |
| 4 W 50° C. | 1 | 6.16 | 9.72 | 95.3 | colorless | clear |
| 4 W 50° C. | 0.5 | 6.22 | 9.74 | 101.5 | colorless | clear |
| 4 W 50° C. | 0.25 | 6.20 | 9.69 | 96.7 | colorless | clear |
| 4 W 50° C. | 0 | 5.94 | 9.76 | 97.2 | yellow | clear |
| 8 W 50° C. | 8 | 6.07 | 9.29 | 96.2 | colorless | clear |
| 8 W 50° C. | 4 | 6.08 | 9.45 | 95 | colorless | clear |
| 8 W 50° C. | 2 | 6.09 | 9.44 | 95.3 | colorless | clear |
| 8 W 50° C. | 1 | 6.02 | 9.47 | 95.3 | straw | clear |
| 8 W 50° C. | 0.5 | 6.05 | 9.45 | 92.8 | straw | clear |
| 8 W 50° C. | 0.25 | 5.95 | 9.53 | 98.6 | straw | clear |
| 8 W 50° C. | 0 | 5.94 | 9.72 | 95.1 | yellow | clear |
| 16 W 50° C. | 8 | 6.12 | 8.78 | 91 | colorless | clear |
| 16 W 50° C. | 4 | 6.11 | 8.99 | 90.4 | colorless | clear |
| 16 W 50° C. | 2 | 6.08 | 9.11 | 92 | straw | clear |
| 16 W 50° C. | 1 | 6.01 | 9.11 | 89.3 | straw | clear |
| 16 W 50° C. | 0.5 | 5.98 | 8.96 | 93.3 | straw | clear |
| 16 W 50° C. | 0.25 | 5.84 | 9.12 | 90.9 | straw | clear |
| 16 W 50° C. | 0 | 5.65 | 9.11 | 90.7 | amber | mod. precip. |

*1,1-Cyclobutanedicarboxylic acid;
3.3 mL of solution per 6 cc Type 1 glass vial with 20 mm teflon-faced stopper., solution adjusted to pH 6 with NaOH.

The addition of even very small amounts of CBDCA to aqueous, 10 mg/mL solutions of carboplatin appeared to have a positive effect on the physical stability of solutions (pH about 6, ~50%, air headspace) at elevated temperatures. As shown in the previous tables, solutions without added CBDCA were amber to brown in color after 4 to 8 weeks at 60° C. or 16 weeks at 50° C. A brown amorphous precipitate was observed. In contrast, solutions of carboplatin with added CBDCA were much lighter in color and displayed no precipitates through 8 weeks at 60° C. or 16 weeks at 50° C.

The lowest level of CBDCA added (0.25 mg/mL) successfully inhibited any visible precipitate formation during the 8 weeks of storage at 60° C. or 16 weeks at 50° C.

As noted in the 4 and 8 week 60° C. data presented in (Table 3) and the 8 and 16 week 50° C. data (Table 4) increasing the CBDCA levels resulted in progressive decrease in intensity of color formation.

At both temperatures, the chemical stability of carboplatin did not appear to be affected by the CBDCA level present. As shown in Table 1, the pH of carboplatin solutions without added CBDCA tended to decrease during the study. However, the pH of solutions containing CBDCA remained very stable. This suggests that presence of added CBDCA (with pH adjustment using NaOH) appeared to have a buffering effect.

Example 2

Effect of Nature of Headspace Gas on Solution Stability (Solutions purged with Gas Indicated)

The effect of nitrogen, oxygen and air on the stability of aqueous solution of carboplatin was examined at 50° C. and 60° C. Solutions of carboplatin were prepared at 10 mg/mL with CBDCA added at 1 mg/mL. The pH was adjusted to 6.0 with 10N and 1N NaOH. Control solutions were prepared at 10 mg/mL (no CBDCA, ambient pH ~6.4).

Aliquots of the solutions were subsequently saturated with either oxygen, air, or nitrogen by bubbling the gases into the solutions for one hour. The purged solutions were filtered into washed #04515/00 Wheaton 6 mL vials (3 mL per vial, 50% fill volume) using a Gelman #4192 sterile 0.2 µm filter. After filling, the remaining headspace was filled with the respective purge gas. Vials were immediately stoppered with Daikyo #759 fluororesin coated stoppers to prevent loss or contamination of headspace gas. All vials were then sealed with Wheaton 20 mm aluminum closures. Samples were stored at 60° C. for 1, 2, 4, and 8 weeks, and at 50° C. for 2, 4, 8, and 16 weeks.

The data for these samples are shown in Tables 5 and 6.

TABLE 5

Effect of Headspace Gas on the Chemical and Physical Stability of Aqueous 10 mg/mL Solutions of Carboplatin at pH 6, ± 1 mg/mL CBDCA*, at 60° C.

| Storage Period (Weeks) | CBDCA | Vial Headspace Gas | pH | Carboplatin mg/mL | % Rem. | Solution Color | Sol. Clarity |
|---|---|---|---|---|---|---|---|
| 0** | yes | Nitrogen | 6.00 | 10.07 | 100 | colorless | clear |
| 0 | yes | Air | 6.00 | 10.18 | 100 | colorless | clear |
| 0 | yes | Oxygen | 6.00 | 10.14 | 100 | colorless | clear |
| 0 | no | Nitrogen | 6.44 | 9.87 | 100 | colorless | clear |
| 0 | no | Air | 6.44 | 9.87 | 100 | colorless | clear |
| 0 | no | Oxygen | 6.44 | 9.87 | 100 | colorless | clear |
| 1 | yes | Nitrogen | 6.10 | 9.93 | 98.5 | amber | clear |
| 1 | yes | Air | 6.10 | 9.77 | 96 | colorless | clear |
| 1 | yes | Oxygen | 6.09 | 10.11 | 99.6 | colorless | clear |
| 1 | no | Nitrogen | 5.82 | 9.63 | 97.5 | brown | brown precip. |
| 1 | no | Air | 5.73 | 9.61 | 97.3 | straw | clear |
| 1 | no | Oxygen | 5.81 | 9.72 | 98.4 | colorless | clear |
| 2 | yes | Nitrogen | 6.07 | 6.32 | 62.8 | colorless | black precip. |
| 2 | yes | Air | 5.95 | 9.54 | 93.7 | straw | clear |
| 2 | yes | Oxygen | 5.98 | 9.60 | 94.6 | colorless | clear |
| 2 | no | Nitrogen | 5.75 | 9.35 | 94.6 | brown | brown precip. |
| 2 | no | Air | 5.93 | 9.37 | 94.9 | yellow | clear |
| 2 | no | Oxygen | 5.97 | 9.59 | 97.1 | straw | clear |
| 4 | yes | Nitrogen | 6.80 | 0.14 | 1.4 | colorless | black precip. |
| 4 | yes | Air | 5.90 | 9.27 | 91 | yellow | clear |
| 4 | yes | Oxygen | 5.89 | 9.45 | 93.3 | straw | clear |
| 4 | no | Nitrogen | 5.56 | 8.80 | 89.1 | brown | brown precip. |
| 4 | no | Air | 5.64 | 8.96 | 90.8 | yellow | clear |
| 4 | no | Oxygen | 5.79 | 8.64 | 88 | straw | clear |
| 8 | yes | Nitrogen | 6.75 | 0.1 | 0.9 | colorless | black precip. |
| 8 | yes | Air | 5.78 | 8.33 | 8.18 | yellow | clear |
| 8 | yes | Oxygen | 5.77 | 8.41 | 82.9 | straw | clear |
| 8 | no | Nitrogen | 5.40 | 7.59 | 76.8 | brownless | brown precip. |
| 8 | yes | Oxygen | 5.77 | 8.41 | 82.9 | straw | clear precip. |
| 8 | no | Nitrogen | 5.40 | 7.59 | 76.8 | brownless | brown precip. |
| 8 | no | Air | 5.57 | 8.26 | 83.6 | amber | light precip. |
| 8 | no | Oxygen | 5.42 | 8.44 | 85.5 | straw | clear |

*1,1-Cyclobutanedicarboxylic acid; 3.3 mL of solution per 6 cc Type I (#4515) glass vial with 20 mm #759 teflon-faced stopper; solution adjusted to pH 6 with NaOH.

TABLE 6

Effect of Headspace Gas on the Chemical and Physical Stability of Aqueous 10 mg/mL Solutions of Carboplatin at pH 6, ± 1 mg/mL CBDCA*, at 50° C.

| Storage Period (Weeks) | CBDCA | Vial Headspace Gas | pH | Carboplatin mg/mL | % Rem. | Solution Color | Sol. Clarity |
|---|---|---|---|---|---|---|---|
| 2 | yes | Nitrogen | 6.35 | 7.53 | 74.8 | colorless | black precip. |
| 2 | yes | Air | 5.94 | 9.68 | 95 | colorless | clear |
| 2 | yes | Oxygen | 5.98 | 9.86 | 96.6 | colorless | clear |
| 4 | yes | Nitrogen | 6.46 | 2.78 | 27.6 | colorless | black precip. |
| 4 | yes | Air | 5.99 | 9.89 | 97.1 | straw | clear |
| 4 | yes | Oxygen | 5.96 | 10.09 | 99.6 | colorless | clear |
| 8 | yes | Nitrogen | 6.80 | 0.21 | 2 | colorless | black precip. |
| 8 | yes | air | 5.95 | 9.34 | 91.6 | straw | clear |
| 8 | yes | Oxygen | 5.93 | 9.53 | 93.9 | colorless | clear |
| 8 | no | Nitrogen | 5.57 | 8.95 | 90.6 | brown | brown precip. |
| 8 | no | Air | 5.70 | 9.18 | 93 | yellow | clear |
| 8 | no | Oxygen | 5.57 | 9.29 | 94.1 | straw | clear |
| 16 | yes | Nitrogen | 7.03 | 0.11 | 1.1 | colorless | black precip. |
| 16 | yes | air | 5.93 | 8.94 | 87.8 | straw | clear |
| 16 | yes | Oxygen | 5.85 | 9.03 | 89 | straw | clear |
| 16 | no | Nitrogen | 6.28 | 2.17 | 22 | colorless | blk & silver precip. |
| 16 | no | Air | 5.60 | 8.75 | 88.6 | yello | light precip. |
| 16 | no | Oxygen | 5.52 | 8.82 | 89.4 | straw | clear |

*1,1-cyclobutane dicarboxylic acid,; 3.3ML of solution per 6 cc Type I (#4515) glass vial with 20 ml #759 "Teflon"-faced stopper; pH6, with NaOH adjustment.

Tables 5 and 6 strongly suggest that vial headspace gas has a significant effect on the physical and chemical stabilities of carboplatin in aqueous solution. Reduced oxygen-:carboplatin ratios created by nitrogen purging of the samples resulted in the appearance of precipitates (insoluble degradation/conversion products) within 1 to 2 weeks at 60° C. (Table 5), and within 4 to 16 weeks at 50° C. (Table 6).

For solutions containing CBDCA, purged with nitrogen and stored at elevated temperatures, there were typically high carboplatin potency losses and supernatant remained colorless (due to precipitation). They contained a heavy, dark black precipitate, characteristic and suggestive of platinum oxides.

Solutions without added CBDCA and similarly purged with nitrogen (devoid of oxygen) usually displayed a fine, brown amorphous precipitate similar in morphology to material identified as an oligomeric mixture that has been observed in solutions stored at lower temperatures (i.e., 4°–30° C.) beyond ~18 months. As shown in Table 4 the nitrogen-purged (devoid of oxygen) solution without added CBDCA stored at 50° C. for 16 weeks showed black and silver precipitates characteristic of platinum oxides and metallic platinum.

Solutions of carboplatin with air headspace (~50% vial fill volume, with or without CBDCA) at 50° C. and 60° C. demonstrated significantly less precipitate formation and much higher carboplatin potency retention than nitrogen-purged (devoid of oxygen) counterparts. Additionally, solutions of carboplatin with air headspace and containing 1 mg/mL CBDCA showed the same reduction in color and prevention or precipitation as was observed in experiments evaluating the effect of CBDCA concentration.

Purging samples with oxygen had a beneficial effect on the physical stability of aqueous, 10 mg/mL carboplatin regardless of the presence or absence of added CBDCA. This is demonstrated by the data in Tables 3 and 4 indicating only slight color formation (i.e., "straw") and the inhibition of any precipitate formation through 8 weeks at 60° C. and 16 weeks at 50° C. Potency retention of Carboplatin appeared comparable for air versus oxygen purged solutions, with or without 1 mg/mL CBDCA.

Example 3

Effect of Vial Fill Volume on Solution Stability

The effect of vial fill volume (i.e., unfilled head space) on the stability of aqueous solutions of carboplatin was also assessed at 50° C. and 60° C. Solutions of carboplatin were prepared at 10 mg/mL (each with 1 mg/ml of CBDCA). The pH was adjusted to 6.0 with 10N and 1N NaOH. Control solutions were prepared at 10 mg/mL (no CBDCA, ambient pH ~5.7).

All solutions were saturated with air by purging (bubbling) with air for one hour. After purging, the solutions were filtered into washed #04514/00 Wheaton 10 mL vials (total capacity is 14 mL) using Gelman #4192 sterile 0.2 μm filters. Vial fill volumes (i.e. total liquid volumes) were 2, 4, 6, 8, 10, and 12 milliliters. The remaining headspace in the vials was filled with air. Vials were stoppered with Daikyo #759 fluororesin coated stoppers and sealed with Wheaton 20 mm aluminum seals. Samples were assayed after 1, 2, 4, and 8 weeks at 60° C.; and 2, 4, 8, and 16 weeks at 50° C.

The data are set out in Tables 7 and 8. Longer term stability samples were placed at lower temperatures (4°, 25°, 40° C.). Initial and stability samples were analyzed chemically and physically.

TABLE 7

Effect of Vial Fill Volume on the 60° C. Chemical and Physical Stability of Aqueous 10 mg/mL Solutions of Carboplatin at pH 6 ± 1 mg/mL CBDCA* With air Headspace ˣ (Air Purged Solutions)

| Storage Period (Weeks) | CBDCA | Liquid Fill Volume (mL) | pH | Carboplatin mg/mL | % Rem | Sol. Color | Sol. Clarity |
|---|---|---|---|---|---|---|---|
| Original | yes | 2 | 6.24 | 9.68 | 100 | colorless | clear |
| Original | yes | 4 | 6.24 | 9.68 | 100 | colorless | clear |
| Original | yes | 6 | | 9.68 | 100 | colorless | clear |
| Original | yes | 8 | | 9.68 | 100 | colorless | clear |
| Original | yes | 10 | 6.24 | 9.68 | 100 | colorless | clear |
| Original | yes | 12 | 6.24 | 9.68 | 100 | colorless | clear |
| Original | no | 2 | 5.67 | 9.88 | 100 | colorless | clear |
| Original | no | 4 | 5.67 | 9.88 | 100 | colorless | clear |
| Original | no | 6 | 5.67 | 9.88 | 100 | colorless | clear |
| Original | no | 8 | 5.67 | 9.88 | 100 | colorless | clear |
| Original | no | 10 | 5.67 | 9.88 | 100 | colorless | clear |
| Original | no | 12 | 5.67 | 9.88 | 100 | colorless | clear |
| 1 | yes | 2 | 6.32 | 9.55 | 98.7 | colorless | clear |
| 1 | yes | 4 | 6.23 | 9.49 | 98.1 | colorless | clear |
| 1 | yes | 6 | 6.20 | 9.48 | 98 | colorless | clear |
| 1 | yes | 8 | 6.15 | 9.55 | 98.6 | colorless | clear |
| 1 | yes | 10 | 6.19 | 9.44 | 97.5 | colorless | clear |
| 1 | yes | 12 | 6.20 | 9.41 | 97.2 | colorless | clear |
| 1 | no | 2 | 5.72 | 9.82 | 99.5 | yellow | clear |
| 1 | no | 4 | 5.77 | 9.77 | 99 | yellow | clear |
| 1 | no | 6 | 5.73 | 9.77 | 98.9 | yellow | clear |
| 1 | no | 8 | 5.74 | 9.76 | 98.8 | yellow | clear |
| 1 | no | 10 | 5.74 | 9.83 | 99.5 | yellow | clear |
| 1 | no | 12 | 5.77 | 9.73 | 98.5 | yellow | clear |
| 2 | yes | 2 | 6.22 | 9.31 | 96.2 | straw | clear |
| 2 | yes | 4 | 6.20 | 9.23 | 95.4 | straw | clear |
| 2 | yes | 6 | 6.20 | 9.21 | 95.2 | straw | clear |
| 2 | yes | 8 | 6.20 | 9.22 | 95.3 | straw | clear |
| 2 | yes | 10 | 6.19 | 9.13 | 94.4 | straw | clear |
| 2 | yes | 12 | 6.20 | 9.11 | 94.1 | straw | clear |
| 2 | no | 2 | 5.75 | 9.54 | 96.6 | yellow | clear |
| 2 | no | 4 | 5.71 | 9.57 | 97.4 | yellow | clear |
| 2 | no | 6 | 5.59 | 9.48 | 96.0 | yellow | clear |
| 2 | no | 8 | 5.65 | 9.41 | 95.2 | yellow | clear |
| 2 | no | 10 | 5.58 | 9.37 | 94.8 | amber | hazy precip. |
| 2 | no | 12 | 5.57 | 9.35 | 94.6 | amber | hazy precip. |
| 4 | yes | 2 | 6.19 | 8.85 | 91.5 | straw | clear |
| 4 | yes | 4 | 6.20 | 8.79 | 90 | straw | clear |
| 4 | yes | 6 | 6.22 | 8.81 | 91 | straw | clear |
| 4 | yes | 8 | 6.17 | 8.73 | 90.3 | yellow | clear |
| 4 | yes | 10 | 6.17 | 8.69 | 89.8 | yellow | clear |
| 4 | yes | 12 | 6.19 | 8.55 | 88.4 | yellow | clear |
| 4 | no | 2 | 5.72 | 9.16 | 92.8 | yellow | clear |
| 4 | no | 4 | 5.71 | 9.06 | 92.2 | yellow | hazy w/light precip. |
| 4 | no | 6 | 5.63 | 9.13 | 92.4 | amber | hazy w/light precip. |
| 4 | no | 8 | 5.61 | 9.05 | 90.4 | brown | mod. precip. |
| 4 | no | 10 | 5.66 | 8.87 | 89.8 | brown | mod. precip. |
| 4 | no | 12 | 6.40 | 4.32 | 43.8 | amber | black + silver precip. |
| 8 | yes | 2 | 5.93 | 7.70 | 79.6 | yellow | clear |
| 8 | yes | 4 | 5.92 | 7.69 | 79.5 | yellow | clear |
| 8 | yes | 6 | 5.89 | 7.67 | 79.3 | yellow | clear |
| 8 | yes | 8 | 5.88 | 7.66 | 79.1 | yellow | clear |
| 8 | yes | 10 | 5.86 | 7.45 | 76.9 | amber | clear |
| 8 | yes | 12 | 6.58 | 0 | 0 | colorless | black precip. |
| 8 | no | 2 | 5.39 | 8.02 | 81.1 | amber | light precip. |
| 8 | no | 4 | 5.32 | 7.96 | 80.6 | amber | light precip. |
| 8 | no | 6 | 5.32 | 7.89 | 79.9 | brown | mod. precip. |
| 8 | no | 8 | 5.26 | 7.76 | 78.5 | brown | heavy brown precip. |
| 8 | no | 10 | 6.43 | 0.68 | 6.9 | colorless | black + silver precip. |
| 8 | no | 12 | 6.43 | 0 | 0 | colorless | black + silver precip. |

CBDCA = 1, 1, cyclobutanedicarboxylic acid
*Solutions in 10 cc. Type 1 glass vials with 20 mm. teflon-faced stopper. Solution pH adjusted to 6 with NaOH.

TABLE 8

Effect of Vial Fill Volume on the 50° C. Chemical and
Physical Stability of Aqueous 10 mg/ml Solutions of
Carboplatin at pH 6 ± 1 mg/mL CBDCA* with Air Headspace[x]

| Storage Period | CBDCA | Vial Fill Volume | pH | Carboplatin Mg/mL | % Rem. | Sol. Color | Sol. Clarity |
|---|---|---|---|---|---|---|---|
| 2 | yes | 2 mL | 6.49 | 9.48 | 97.9 | colorless | clear |
| 2 | yes | 4 mL | 6.49 | 9.53 | 98.5 | colorless | clear |
| 2 | yes | 6 mL | 6.48 | 9.55 | 98.6 | colorless | clear |
| 2 | yes | 8 mL | 6.31 | 9.52 | 98.4 | colorless | clear |
| 2 | yes | 10 mL | 6.29 | 9.53 | 98.5 | colorless | clear |
| 2 | yes | 12 mL | 6.31 | 9.48 | 98 | colorless | clear |
| 2 | no | 2 mL | 6.13 | 9.9 | 100.2 | straw | clear |
| 2 | no | 4 mL | 6.1 | 9.82 | 99.4 | straw | clear |
| 2 | no | 6 mL | 6.05 | 9.49 | 95.7 | straw | clear |
| 2 | no | 8 mL | 5.92 | 9.79 | 99.1 | straw | clear |
| 2 | no | 10 mL | 6.02 | 9.8 | 99.2 | straw | clear |
| 2 | no | 12 mL | 6.1 | 9.84 | 99.6 | straw | clear |
| 4 | yes | 2 mL | 6.29 | 9.48 | 98 | colorless | clear |
| 4 | yes | 4 mL | 6.21 | 9.43 | 97.5 | colorless | clear |
| 4 | yes | 6 mL | 6.27 | 9.39 | 97.1 | colorless | clear |
| 4 | yes | 8 mL | 6.32 | 9.45 | 97.7 | colorless | clear |
| 4 | yes | 10 mL | 6.03 | 9.5 | 98.2 | colorless | clear |
| 4 | yes | 12 mL | 6.30 | 9.49 | 98.1 | colorless | clear |
| 4 | no | 2 mL | 6.10 | 9.83 | 99.5 | straw | clear |
| 4 | no | 4 mL | 6.23 | 9.79 | 99.1 | straw | clear |
| 4 | no | 6 mL | 6.05 | 9.69 | 98.1 | straw | clear |
| 4 | no | 8 mL | 5.91 | 9.74 | 98.7 | yellow | clear |
| 4 | no | 10 mL | 5.98 | 9.71 | 98.3 | yellow | clear |
| 4 | no | 12 mL | 5.94 | 9.71 | 98.4 | yellow | clear |
| 8 | yes | 2 mL | 6.22 | 9.09 | 93.9 | straw | clear |
| 8 | yes | 4 mL | 6.20 | 9.10 | 94.1 | straw | clear |
| 8 | yes | 6 mL | 6.17 | 9.09 | 93.9 | straw | clear |
| 8 | yes | 8 mL | 6.17 | 9.06 | 93.7 | straw | clear |
| 8 | yes | 10 mL | 6.15 | 9.05 | 93.5 | straw | clear |
| 8 | yes | 12 mL | 6.14 | 9.09 | 94 | straw | clear |
| 8 | no | 2 mL | 5.93 | 9.50 | 96.2 | yellow | clear |
| 8 | no | 4 mL | 6.06 | 9.29 | 94 | yellow | clear |
| 8 | no | 6 mL | 5.75 | 9.30 | 94.2 | yellow | light precip. |
| 8 | no | 8 mL | 5.66 | 9.39 | 95.1 | yellow | light precip. |
| 8 | no | 10 mL | 5.63 | 9.34 | 94.5 | amber | light precip. |
| 8 | no | 12 mL | 5.62 | 9.34 | 94.6 | amber | light precip. |
| 16 | yes | 2 mL | 6.07 | 8.67 | 89.6 | straw | clear |
| 16 | yes | 4 mL | 6.07 | 8.67 | 89.6 | straw | clear |
| 16 | yes | 6 mL | 6.07 | 8.66 | 89.5 | straw | clear |
| 16 | yes | 8 mL | 6.07 | 8.63 | 89.2 | yellow | clear |
| 16 | yes | 10 mL | 6.10 | 8.65 | 89.4 | yellow | clear |
| 16 Weeks/°C. | yes | 12 mL | 6.11 | 8.67 | 89.6 | yellow | clear |
| 16/50° C. | no | 2 mL | 5.56 | 9.08 | 92 | yellow | hazy w/precip. |
| 16/50° C. | no | 4 mL | 5.52 | 9.04 | 91.4 | yellow | light precip. |
| 16/50° C. | no | 6 mL | 5.47 | 8.96 | 90.7 | yellow | light precip. |
| 16/50° C. | no | 8 mL | 5.43 | 8.92 | 90.4 | amber | moderate precip. |
| 16/50° C. | no | 10 mL | 5.41 | 8.89 | 90 | amber | moderate precip. |
| 16/50° C. | no | 12 mL | 5.40 | 8.87 | 89.8 | brown | heavy precip. |

*1, 1-cyclobutanedicarboxylic acid
[x]Solutions in 10 cc Type I glass vials with 20 mm teflon-faced stopper, solution adjusted to pH 6 with NaOH.
Total vial volume is 14 mL.

The amount of precipitate formed in aqueous, 10 mg/mL Carboplatin solutions (no added CBDCA, initial ambient pH ~5.7) at 50° C. and 60° C. was directly related to the volume of solution filled into the 10 cc vial (actual maximum fill capacity ~14 mL). As fill volume increased (with corresponding decrease in oxygen: carboplatin ratio), both color intensity and amount of precipitates increased. This suggests that stability of carboplatin is correlated with amounts (ratio) of oxygen present, demonstrating the effect of headspace gas on stability.

Data in Table 6 show a high vial fill volume (lowered availability of oxygen) of 10–12 mL of solution (no added CBDCA) resulted in extensive potency losses after 8 weeks at 60° C., with formation of black and silver precipitate (suggestive of platinum oxides and metallic platinum).

Solutions of carboplatin containing no added CBDCA stored at 50° C. and 60° C. exhibited precipitate at all fill volumes (time of precipitate formulation appears earlier and amounts present are greater with increased temperature or fill volume). Except for vials with very high fill volume (i.e., 10–12 mL), the precipitate formed at 50° C. and 60° C. was predominantly the brown, amorphous type typical of an oligomeric mixture. Small amounts of circular, "maltese cross"-type crystals were also observed in many of the degraded samples.

Example 4

Effect of pH on Solution Stability (Air Purged Solutions)

The effect of pH on the aqueous solution stability of 10 mg/mL carboplatin was studied at 50° C. and 60° C. A level of 1 mg/mL CBDCA was added to each solution. The pH of the solutions was adjusted to 4, 5, 6, 7, and 8 with 1N and 10N NaOH. The effect of pH on solutions without added CBDCA was not examined due to the difficulty in adjusting the pH without converting carboplatin to other compounds (e.g., adding HCl could convert to cisplatin).

Each solution was purged by bubbling with air for one hour, then filtered into washed #04515/00 Wheaton 6 mL vials using Gelman #4192 0.2 μm sterile filters. Each vial was filled with three milliliters (50% fill volume) of carboplatin solution. The remaining vial headspace was air.

The vials were stoppered with Daikyo #759 fluororesin coated stoppers and sealed with Wheaton 20 mm aluminum closures. Samples were stored at 60° C. for 1, 2, 4, and 8 weeks and at 50° C. for 2, 4, 8, and 16 weeks. The data for these samples are given in Table 9.

TABLE 9

Effect of pH on the Chemical and Physical Stability of Aqueous, 10 mg/mL solutions of Carboplatin Containing 1 mg/mL CBDCA With Air Headspace[x]

| Storage Conditions | pH | Carboplatin mg/mL | % Rem. | Solution Color | Sol. Clarity |
|---|---|---|---|---|---|
| Original | 4.02 | 10.43 | 100 | colorless | clear |
| Original | 5.00 | 10.45 | 100 | colorless | clear |
| Original | 6.06 | 10.36 | 100 | colorless | clear |
| Original | 7.06 | 10.24 | 100 | colorless | clear |
| Original | 8.00 | 9.73 | 100 | colorless | clear |
| 1 W 60° C. | 3.82 | 9.41 | 90.2 | straw | clear |
| 1 W 60° C. | 4.89 | 10.3 | 98.6 | colorless | clear |
| 1 W 60° C. | 5.94 | 10.1 | 97.5 | colorless | clear |
| 1 W 60° C. | 6.72 | 9.83 | 96 | colorless | clear |
| 1 W 60° C. | 7.00 | 8.92 | 91.6 | colorless | clear |
| 2 W 60° C. | 4.12 | 10.38 | 99.5 | yellow | clear |
| 2 W 60° C. | 5.06 | 10.14 | 97.1 | straw | clear |
| 2 W 60° C. | 6.10 | 9.95 | 96.1 | straw | clear |
| 2 W 60° C. | 6.70 | 9.53 | 93.1 | straw | clear |
| 2 W 60° C. | 6.81 | 8.67 | 89.1 | straw | clear |
| 4 W 60° C. | 4.30 | 9.24 | 88.5 | amber | clear |
| 4 W 60° C. | 5.12 | 9.62 | 92.1 | yellow | clear |
| 4 W 60° C. | 6.07 | 9.20 | 88.8 | straw | clear |
| 4 W 60° C. | 6.53 | 8.71 | 85.1 | straw | clear |
| 4 W 60° C. | 6.64 | 7.59 | 77.9 | straw | clear |
| 8 W 60° C. | 4.54 | 9.43 | 90.4 | brown | clear |
| 8 W 60° C. | 5.20 | 9.20 | 88.1 | amber | clear |
| 8 W 60° C. | 6.03 | 8.42 | 81.3 | yellow | clear |
| 8 W 60° C. | 6.44 | 7.98 | 77.9 | yellow | clear |
| 8 W 60° C. | 6.56 | 7.14 | 73.4 | amber | clear |
| 2 W 50° C. | 4.00 | 10.32 | 99 | straw | clear |
| 2 W 50° C. | 5.06 | 10.38 | 99.4 | colorless | clear |
| 2 W 50° C. | 6.12 | 10.36 | 100 | colorless | clear |
| 2 W 50° C. | 6.98 | 10.17 | 99.3 | colorless | clear |
| 2 W 50° C. | 7.49 | 9.60 | 98.7 | colorless | clear |
| 4 W 50° C. | 4.05 | 10.01 | 96 | yellow | clear |
| 4 W 50° C. | 5.03 | 9.44 | 90.4 | straw | clear |
| 4 W 50° C. | 6.09 | 10.03 | 96.8 | colorless | clear |
| 4 W 50° C. | 6.77 | 9.75 | 95.1 | colorless | clear |
| 4 W 50° C. | 7.18 | 9.10 | 93.5 | colorless | clear |
| 8 W 50° C. | 4.05 | 10.01 | 95.9 | yellow | clear |
| 8 W 50° C. | 5.03 | 10.00 | 95.8 | straw | clear |
| 8 W 50° C. | 6.09 | 9.81 | 94.8 | colorless | clear |
| 8 W 50° C. | 6.77 | 9.43 | 92.2 | colorless | clear |
| 8 W 50° C. | 7.18 | 8.88 | 91.2 | straw | clear |
| 16 W 50° C. | 4.53 | 9.73 | 93.3 | amber | clear |
| 16 W 50° C. | 5.16 | 9.67 | 92.6 | yellow | clear |
| 16 W 50° C. | 6.06 | 9.68 | 93.5 | straw | clear |
| 16 W 50° C. | 6.55 | 8.80 | 85.9 | straw | clear |
| 16 W 50° C. | 6.73 | 8.23 | 84.5 | straw | clear |

[x]W = week(s)
3.3 mL of solution per 6 cc. Type I glass vial with 20 mm teflon-faced stopper, solutions adjusted to various pH with NaOH.

The effect of pH on the chemical and physical stability of aqueous, 10 mg/mL solutions of Carboplatin (~50% vial fill volume as air headspace) containing 1 mg/mL of added CBDCA is presented in Table 7. Independent of starting pH (i.e., at pH 4–8), all solutions remained clear and precipitate-free through 8 weeks at 60° C. or 16 weeks at 50° C., confirming the positive effect of added CBDCA on physical stability.

The color of solutions stored at elevated temperatures appeared most intense at the lowest initial pH studied (pH 4). The least color formation was noted for the initial pH 6–7 samples.

Chemical stability (carboplatin potency retention) appeared to decrease slightly as pH was increased from 4 to 8 (most evident for the 8 and 16 week 50° C. data, and 8 week 60° C. data). For the initial pH 4–7 solutions, the pH of the degraded samples remained relatively unchanged (i.e., <0.5 pH unit change). Based on the physical and chemical data obtained from these preliminary studies, a formulation pH of 4 to 7 appears optimal for overall chemical and physical stability.

Overall Results

The data presented herein demonstrates that CBDCA and purging with air or oxygen and maintenance of a significant (i.e., 10 volume % percent to 50 volume % or greater) of air or oxygen in the container head space yields storable carboplatin solutions having satisfactory chemical and physical stability. Their stability is evidenced by the fact that the solutions exhibit minimal color formation (generally, clear, amber, yellow or green) and no or little formation of solid precipitate.

Buffering, or pH maintenance, with sodium hydroxide and, optionally, CBDCA is beneficial. CBDCA concentrations of 5–40% of the concentration of carboplatin inhibit the formation of color and precipitate.

Reasonable variations, such as those which would occur to a skilled artisan, can be made herein without departing from the scope of the invention.

We claim:

1. A chemically and physically stable injectable composition of a malonato platinum (II) compound comprising:

(a) an antitumor effective amount of a platinum(II) compound of Formula I:

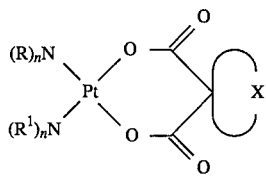

wherein:
R and R' are independently selected from H, $C_{1-6}$ alkyl, $C_{1-6}$ hydroxyalkyl, $C_{5-12}$ aryl, $C_{5-12}$ alkaryl $C_{5-12}$ aralkyl, $C_{1-6}$ alkoxyalkyl and $C_{5-12}$ amino acid residues;
n is 2 or 3; and
X is the residue of a cyclic $C_{3-6}$ alkyl or alkenyl group;

(b) a stabilizing amount of 1,1-cyclobutanedicarboxylic acid or an alkali metal salt thereof;

(c) sufficient pH modifier to maintain a pH of about 4 to about 7; and (d) a pharmaceutically acceptable carrier.

2. The composition of claim 1 wherein the pH modifier is the sodium salt of 1,1-cyclobutanedicarboxylic acid.

3. The composition of claim 2 wherein the amount of (a) is from about 1 to about 20 mg/ml.

4. The composition of claim 2 wherein the amount of (b) is from 0.25 to about 4 mg/ml.

5. The composition of claim 3 wherein (d) is selected from the group consisting of: water, polyalkylene glycols containing $C_{1-6}$ alkyl groups, aqueous dextrose solution and mixtures thereof.

6. The composition of claim 2 wherein (d) is water.

7. The composition of claim 5 wherein (a) is carboplatin.

8. The composition of claim 1 in which the solution is purged with air or oxygen after it is mixed.

9. A method of stabilizing a solution of a malonato platinum(II) compound selected from carboplatin or a malonato congener comprising:

(1) adding a stabilizing amount of 1,1-cyclobutanedicarboxylic acid (or a corresponding malonato congener) or an alkali metal salt thereof to the solution, and (2) adjusting the pH and maintaining it at about 4 to about 7.

10. The method of claim 9 wherein the amount of 1,1-cyclobutanedicarboxylic acid or salt employed is from about 0.25 to about 20 mg/ml.

11. The method of claim 9 wherein the amount of acid or salt present is from about 1 to about 20 mg/ml.

12. The method of claim 10 wherein the solution is purged with air or oxygen after it is mixed.

13. The method of claim 11 wherein the final solution is stored in a sealed container in which the headspace volume is 50% or more.

14. The method of claim 13 wherein the headspace is blanketed with air or oxygen before the container is sealed.

15. The method of claim 11 wherein, as a subsequent step (3), the solution is purged with air or oxygen.

16. A process for stabilizing a malonato platinum(II) compound of a solution comprising the steps of:

(1) dissolving the platinum compound in a carrier and adjusting the pH to about 4 to about 7, (2) purging the product of step (1) with at least one of air or oxygen gas, and (3) placing the purged solution into a container so that at least 50 volume % is unfilled with liquid, but saturated with air or oxygen.

* * * * *